United States Patent [19]

Bank

[11] Patent Number: 5,262,554
[45] Date of Patent: * Nov. 16, 1993

[54] PROCESS FOR PREPARATION OF BETA-CYANOALKYLSILANES

[75] Inventor: Howard M. Bank, Freeland, Mich.

[73] Assignee: Dow Corning Corporation, Midland, Mich.

[*] Notice: The portion of the term of this patent subsequent to Sep. 21, 2010 has been disclaimed.

[21] Appl. No.: 998,323

[22] Filed: Dec. 30, 1992

[51] Int. Cl.$^5$ .............................................. C07F 7/10
[52] U.S. Cl. .................................. 556/415; 556/479
[58] Field of Search ...................................... 512/415

[56] References Cited

U.S. PATENT DOCUMENTS

| | | | |
|---|---|---|---|
| 2,823,218 | 2/1958 | Speier | 556/415 |
| 2,860,153 | 11/1958 | Saam | 556/415 |
| 2,906,764 | 9/1959 | Jex et al. | 260/448.2 |
| 2,906,765 | 9/1959 | Jex et al. | 556/415 |
| 2,907,784 | 10/1959 | Jex et al. | 556/415 |
| 2,908,699 | 10/1959 | Jex et al. | 556/415 |
| 3,257,440 | 6/1966 | Jex et al. | 556/415 |
| 4,614,812 | 9/1986 | Schilling | 556/415 X |
| 5,103,033 | 4/1992 | Bank | 556/415 |
| 5,126,468 | 6/1992 | Bank | 556/415 |
| 5,126,469 | 6/1992 | Bank | 556/415 |

OTHER PUBLICATIONS

Pike et al., J. Org. Chem. 24, 1939–42, 1959.
Pike et al., J. Org. Chem. 27, 2190–92, 1962.

*Primary Examiner*—Paul F. Shaver
*Attorney, Agent, or Firm*—William F. Boley

[57] ABSTRACT

The present invention is a process for the preparation of hydrolyzable beta-cyanoalkylsilanes. More particularly, this invention relates to the catalytic addition of silicon hydrides to alpha,beta-unsaturated olefinic nitriles to form beta-cyanoalkylsilanes. The present invention employs a novel catalyst comprising a supported aminoorganosilane.

26 Claims, No Drawings

PROCESS FOR PREPARATION OF BETA-CYANOALKYLSILANES

BACKGROUND OF INVENTION

The present invention is a process for the preparation of hydrolyzable beta-cyanoalkylsilanes. More particularly, this invention relates to the catalytic addition of silicon hydrides to alpha,beta-unsaturated olefinic nitriles to form beta-cyanoalkylsilanes. The present invention employs a novel catalyst comprising a supported aminoorganosilane.

Hydrolyzable beta-cyanoalkylsilanes are useful for the production of polyorganosiloxanes containing the beta-cyanoalkyl substituent. The silicon-bonded beta-cyanoalkyl radical is extremely resistant to hydrolysis and cleavage under hot, humid conditions. Therefore, the beta-cyanoalkylsilanes find particular use in the preparation of polyorganosiloxanes which must be subjected to hot, humid conditions. The presence of the silicon-bonded beta- cyanoalkyl radical substituted on polyorganosiloxanes also tends to stabilize the polyorganosiloxanes against swelling induced by liquid hydrocarbons.

Jex et al., U.S. Pat. No. 2,906,764, issued Sep. 29, 1959, describe a process for producing cyanoalkylsilanes by reacting an olefinic nitrile with a silane, the silane having at least one hydrogen and one hydrolyzable group bonded to the silicon atom, in the presence of a diarylamine catalyst.

Pike et al., J. Org. Chem. 24, 1939-42, 1959, describe tertiary amines as effective directive catalysts for the reaction of trichlorosilane with acrylonitrile to form beta-cyanoethyltrichlorosilane.

Pike et al., J. Org. Chem. 27, 2190-92, 1962, describe preparation of beta-cyanoethyltrichlorosilane by reacting trichlorosilane with acrylonitrile in the presence of silylamine catalysts of the general formula $(CH_3)_3SiNR_2$, where the nitrogen atom of the silylamine is attached to the silicon atom. Pike et al. postulate that some of the amino groups from these silylamines probably rearrange with the chloro groups of the trichlorosilane to form a silylamine of formula $HSi(NR_2)Cl_2$, which silylamine may be the actual catalyst for the reaction of trichlorosilane with acrylonitrile.

The present process employs a novel catalyst comprising a supported aminoorganosilane. "Supported aminoorganosilane" means an aminoorganosilane which is retained on a solid support. The amino radical of the aminoorganosilane is attached to a carbon radical which is in turn attached to silicon through a silicon-carbon linkage. These supported aminoorganosilanes promote the beta-hydrosilylation of unsaturated olefinic nitriles by silicon hydrides.

SUMMARY OF INVENTION

The present invention is a process for the preparation of hydrolyzable beta-cyanoalkylsilanes. More particularly, this invention relates to the catalytic addition of silicon hydrides to alpha,beta-unsaturated olefinic nitriles to form beta-cyanoalkylsilanes. The present invention employs a novel catalyst comprising a supported aminoorganosilane.

DESCRIPTION OF INVENTION

The present invention is a process for preparation of beta-cyanoalkylsilanes described by formula:

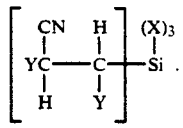  (1)

The process comprises contacting a silicon hydride described by formula $$HSiX_3 \qquad (2)$$

with an unsaturated olefinic nitrile described by formula $$YCH\!=\!CCN, \qquad (3)$$

in the presence of a catalyst comprising an aminoorganosilane described by formula

  (4)

$$R_a(RO)_bSi(R^1NR^2)_c,$$

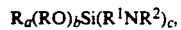

which is retained on a solid support;
at a temperature within a range of about 50° C. to 250° C.; where each R is independently selected from a group consisting of monovalent hydrocarbon radicals of 1 to 20 carbon atoms; each $R^1$ is independently selected from a group consisting of bivalent hydrocarbon radicals of 1 to 20 carbon atoms; each $R^2$ is independently selected from a group consisting of hydrogen, monovalent hydrocarbon radicals of 1 to 20 carbon atoms, aminoalkyl radicals, alkylaminoalkyl radicals, alkylaminodialkyl radicals, dialkylaminoalkyl radicals, and polyaminoalkyl radicals; X is a halogen; each Y is independently selected from a group consisting of hydrogen and lower alkyl radicals of 1 to 8 carbon atoms; a=0, 1, 2, or 3; b=0, 1, 2, or 3; c=1, 2, 3, or 4; and a+b+c=4.

The described process is applicable to the production of beta-cyanoalkylsilanes containing one silicon-bonded beta-cyanoalkyl radical, as described by Formula 1. Beta-cyanoalkylsilanes that can be made by the present process are, for example, beta-cyanoethyltrichlorosilane, beta-cyanopropyltrichlorosilane, beta-cyanobutyltrichlorosilane, beta-cyano-tert-butyltrichlorosilane, beta-cyanopentyltrichlorosilane, beta-cyanopropyltrichlorosilane, beta-cyanohexyltrichlorosilane, beta-cyanoheptyltrichlorosilane, beta-cyanooctyltrichlorosilane, alpha-methyl-beta-cyanoethyltrichlorosilane, alpha-ethyl-beta-cyanoethyltrichlorosilane, alpha-octyl-beta-cyanopropyltrichlorosilane, beta-cyanoethyltribromosilane, and beta-cyanopropyltrifluorosilane. The preferred beta-cyanoalkylsilane that can be made by the present process is beta-cyanoethyltrichlorosilane.

The silicon hydride, described by Formula 2, contains one silicon-bonded hydrogen atom and three silicon-bonded halogen atoms. The halogen atom, X, can be selected from a group consisting of bromine, chlorine, fluorine, and iodine. The preferred halogen is chlorine.

The silicon hydride is contacted with an alpha,beta-unsaturated olefinic nitrile described by Formula 3. The unsaturated olefinic nitrile contains substituents Y which are independently selected from a group consisting of hydrogen and lower alkyl radicals. The term "lower alkyl radicals" means alkyl radicals comprising from 1 to 8 carbon atoms. For example, Y can be methyl, ethyl, propyl, butyl, tert-butyl, pentyl, hexyl, heptyl, and octyl. Examples of the unsaturated olefinic nitrile include acrylonitrile, methacrylonitrile, crotononitrile, ethylacrylonitrile, 1- cyanobutene-1, or 2-cyanooctene-1. The preferred unsaturated olefinic nitrile is acrylonitrile.

The molar ratio of the silicon hydride to the unsaturated olefinic nitrile may be varied within wide limits, however, no particular advantage is derived from employing a molar excess of either reactant. The use of molar excesses of either of the two reactants is not precluded. It is preferred that the molar ratio of silicon hydride to unsaturated olefinic nitrile is within a range of about 0.5 to 1.5. In the most preferred embodiment of the invention, the molar ratio of silicon hydride to unsaturated olefinic nitrile is about 1.0.

The silicon hydride and unsaturated olefinic nitrile are contacted in the presence of a catalyst comprising an aminoorganosilane. The aminoorganosilane is described by Formula 4, i.e., $R_a(RO)_bSi(R^1NR^2_2)_c$, where each R is independently selected from a group consisting of monovalent hydrocarbon radicals of 1 to 20 carbon atoms; each $R^1$ is independently selected from a group consisting of bivalent hydrocarbon radicals of 1 to 20 carbon atoms; each $R^2$ is independently selected from a group consisting of hydrogen, monovalent hydrocarbon radicals of 1 to 20 carbon atoms, aminoalkyl radicals, alkylaminoalkyl radicals, alkylaminodialkyl radicals, dialkylaminoalkyl radicals, and polyaminoalkyl radicals; $a=0, 1, 2,$ or 3; $b=0, 1, 2,$ or 3; $c=1, 2, 3,$ or 4; and $a+b+c=4$.

Each radical R of the aminoorganosilane is independently selected from a group consisting of monovalent hydrocarbon radicals of 1 to 20 carbon atoms. The radical R can be alkyl, for example, methyl, ethyl, propyl, iso-propyl, butyl, tert-butyl, pentyl, hexyl, heptyl, octyl, and eicosyl. The preferred alkyl radical is when R is a lower alkyl radical containing from one to eight carbon atoms. The radical R can also be aryl radicals, for example, phenyl, naphthyl, diphenyl, tolyl, xylyl, cumenyl, ethylphenyl and vinylphenyl. The preferred aryl radical is phenyl. The radical R can be aralkyl, for example, benzyl and phenylethyl; cyanoalkyl, for example beta-cyanoethyl, beta-cyanopropyl, and beta-cyanobutyl; cycloalkyl, for example cyclopentyl, cyclohexyl, and cycloheptyl; and alkenyl, for example vinyl and allyl.

Each radical $R^1$ of the aminoorganosilane is independently selected from a group consisting of bivalent hydrocarbon radicals of 1 to 20 carbon atoms. Examples of radical $R^1$ of the aminoorganosilane include bivalent alkylene radicals, for example, methylene, ethylene, propylene, isopropylene, butylene, iso-butylene, tert-butylene, pentylene, hexamethylene, heptamethylene, octamethylene, and eicosamethylene. The radical $R^1$ can also be bivalent alkenylene radicals, for example, ethenylene, propenylene, tert-butenylene, and eicosenylene; bivalent cyclic radicals, for example, cyclopropylene, cyclopropylidene, and cyclobutylene; bivalent arylene radicals, for example, phenylene, napthalenylene, phenanthrylene.

Each radical $R^2$ is independently selected from a group consisting of hydrogen, monovalent hydrocarbon radicals of 1 to 20 carbon atoms, aminoalkyl radicals, alkylaminoalkyl radicals, alkylaminodialkyl radicals, dialkylaminoalkyl radicals, and polyaminoalkyl radicals. Examples of radical $R^2$ of the aminoorganosilane include hydrogen and the examples of monovalent hydrocarbon radicals provided for radical R of the aminoorganosilane.

Radical $R^2$ can also be aminoalkyl radicals, for example, aminomethyl, and aminopropyl; alkylaminoalkyl radicals, for example, N'-methylaminomethyl, N'-methylaminoethyl, N'-ethylaminoethyl, N'-ethylaminomethyl, and N'-methylaminohexamethyl; alkylaminodialkyl radicals, for example a radical with the structure

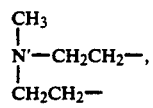

which would bond with N of the aminoorganosilane to form an $NR^2$ radical which was methylpiperazinyl; dialkylaminoalkyl, for example, N',N'-dimethylaminomethyl, N',N'-dimethylaminoethyl, N',N',-diethylaminomethyl, N'- methyl-N'-ethylaminoethyl, N',N'-dimethylaminopropyl, and N'- methyl-N'-octylaminoethyl. The radicals $R^2$ can also be polyaminoalkyl, which can be described by the formula ${(CH_2)_eN(B)}_fA$, where A is independently selected from a group consisting of hydrogen and lower alkyl radicals, B is independently selected from a group consisting of hydrogen and lower alkyl radicals, e is an integer from 1 to 6, and f is an integer from 1 to 20. Examples of the $R^2$ polyalkylamino radicals include N'',N''-dimethylaminoethyl-N'- methylaminoethyl, N'',N''-dimethylaminoethylaminoethyl, N''- methylaminoethyl-N'-methylaminoethyl, N'''-ethylaminoethyl-N'- ethylaminoethyl, and N'''-methylaminopropyl-N'- methylaminopropyl.

The preferred radicals $R^2$ are methyl, and N',N'-dimethylaminoethyl. Most preferred is when one radical $R^2$ is methyl and the second radical $R^2$ is N',N'-dimethylaminoethyl. In the examples above, the primes denoting the location of pendant groups on the nitrogen atoms of the radicals $R^2$ are numbered as they would be numbered in the aminoorganosilane according to the nomenclature used below to describe examples of the aminoorganosilane.

Examples of the aminoorganosilane include N-methylaminopropyltrimethoxysilane{i.e., $(CH_3O)_3SiCH_2CH_2CH_2N(H)CH_3$}, N,N-dimethylaminopropyltrimethoxysilane, N',N'-dimethylaminoethylaminopropyltrimethoxysilane {i.e.,$(CH_3O)_3SiCH_2CH_2CH_2N(H)CH_2CH_2N(CH_3)_2$}, N,N-dimethylaminoethylmethyldimethoxysilane{i.e., $(CH_3O)_2CH_3SiCH_2CH_2N(CH_3)_2$}, N',N'-dimethylaminoethyl-N-methylaminopropyltrimethoxysilane ${(CH_3O)_3SiCH_2CH_2CH_2N(CH_3)CH_2CH_2N(CH_3)_2}$, N',N'-dimethylaminopropyl-N-methylaminopropyltrimethoxysilane, N',N'-dimethylaminoethyl-N- methylaminopropyltrimethylsilane, N'''-methylaminoethyl-N'-methylaminoethyl-N-methylaminoethyltrimethoxysilane {i.e., $(CH_3O)_3SiCH_2CH_2N(CH_3)CH_2CH_2N(CH_3)CH_2CH_2N(H)CH_3$}, N'',N''-diethylaminoethyl-N'-ethylaminoethylaminopropyl-methyldimethoxysilane {i.e., $(CH_3O)_2CH_3SiCH_2CH_2CH_2N(H)CH_2CH_2N(CH_2CH_3)CH_2CH_2N(CH_2CH_3)_2$}, N',N'-dimethylaminoethyl-N-methylaminobutyltrimethoxysilane, N',N'-dimethylaminoethyl-N-methylaminoethylmethyldimethoxysilane, N',N'-dimethylaminoethyl-N- methylaminoisobutylmethyldimethoxysilane, piperazinylpropyltrimethoxysilane, N",N"-dimethylaminobutyl-N'-methylaminobutylaminobenzyltrimethylsilane, N',N'-dimethylaminomethylaminophenylethyltrimethoxysilane {i.e., (CH$_3$O)$_3$SiCH$_2$CH$_2$C$_6$H$_4$-N(H)CH$_2$N(CH$_3$)$_2$, N-methylaminohexamethylmethyldimethoxysilane, N'-methyl-N-piperazinylpropylmethyldimethoxysilane, and N'-methyl-N-piperazinylpropyltrimethoxysilane. The preferred aminoorganosilanes are: N,N-dimethylaminopropyltrimethoxysilane, i.e, (CH$_3$O)$_3$SiCH$_2$CH$_2$CH$_2$N(CH$_3$)$_2$; N-methylaminopropyltrimethoxysilane, i.e., (CH$_3$O)$_3$-SiCH$_2$CH$_2$CH$_2$N(H)CH$_3$; N'-methyl-N-piperazinylpropylmethyldimethoxysilane,

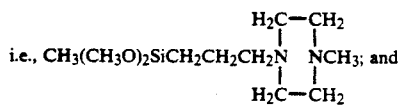

i.e., CH$_3$(CH$_3$O)$_2$SiCH$_2$CH$_2$CH$_2$N⌐NCH$_3$; and

N',N'-dimethylaminoethyl-N-methylaminopropyltrimethoxysilane, i.e., CH$_3$O)$_3$-SiCH$_2$CH$_2$CH$_2$N(CH$_3$)CH$_2$CH$_2$N(CH$_3$)$_2$. The most preferred aminoorganosilane is N',N'-dimethylaminoethyl-N-methylaminopropyltrimethoxysilane.

The aminoorganosilane is retained on a solid support. The method of retention of the aminoorganosilane on the solid support is not critical to the present invention. It is preferred that the aminoorganosilane not be released from the solid support during conduct of the process. The aminoorganosilane may be retained on the solid support by standard means, for example, adsorption, ionic bonding, covalent bonding, or physical entrapment. The preferred method of retention of the aminoorganosilane is covalent bonding.

The solid support can be any material capable of retaining the aminoorganosilane under process conditions. The solid support can be, for example, silica gel, aluminum oxide, mixtures of aluminum oxide and chromium oxide, sodium zeolite, mixtures of aluminum oxide and tungsten oxide, magnesium oxide, zinc oxide, titanium oxide, asbestos, magnesium silicate, aluminum silicate, calcium silicate, and glass. The preferred solid support is silica gel.

The solid support can be in the form of, for example, flakes, chips, particles, powders, pellets, and tablets. It is preferred that the solid support be less than about one centimeter in diameter. It is more preferred that the solid support be less than about 0.5 centimeter in diameter. The lower size limit for the solid support is determined by the practicalities of retaining, recovering, and handling of the material. When the process employs a fixed catalyst bed, it is preferred that the particle size of the solid support be sufficient to allow liquid to flow through the bed.

A useful concentration of aminoorganosilane retained on the solid support is where the weight of aminoorganosilane is within a range of about 0.1 to 50 weight percent of the weight of the solid support. Lower concentrations of aminoorganosilanes may be used, but the production rate of the beta-cyanoalkylsilane may be reduced.

The amount of the aminoorganosilane employed in relation to the amount of the unsaturated olefinic nitrile may be varied within wide limits. In general, the process can be run under conditions where the molar ratio of the aminoorganosilane to the unsaturated olefinic nitrile is in a range of about 0.001 to 5.0. A preferred molar ratio of the aminoorganosilane to the unsaturated olefinic nitrile is in a range of about 0.010 to 0.7.

Although not necessary, the solid support of the supported aminoorganosilane can be silylated. The preferred silylating agent is hexamethyldisilazane.

The silicon hydride, the unsaturated olefinic nitrile and the supported aminoorganosilane are contacted in a suitable reactor of standard design. The type of reactor is not critical. The process can be run as a batch process, a semi-batch process, or a continuous process. A preferred process is where the reaction is conducted under heterogeneous conditions in a continuous-flow pressure coil with a fixed catalyst bed.

Although not necessary, it is preferred that the contents of the reactor be mixed when the process is run as a batch process. Mixing can be accomplished by standard means, for example, mechanical stirring, refluxing, sonification, or turbulent flow.

It is preferred that the process be conducted in an essentially oxygen free environment. By "free oxygen," it is meant oxygen that is not present in combination with other elements. The term "essentially oxygen free environment" means the free oxygen content of the environment in which the process is run is reduced below that of normal air. It is preferred that the essentially oxygen free environment contain less than about 0.5 percent free oxygen.

Where the process is run in an essentially oxygen free environment, it is preferred that the reactor be of a type that allows free oxygen to be essentially eliminated from contact with the silicon hydride, the unsaturated olefinic nitrile, and the catalyst. The reactor can be reduced in free oxygen by standard means, for example, purging with an inert gas such as nitrogen, argon, or helium or by vacuum evacuation. Preferred is when the reactor is purged with inert gas prior to addition of reactants and catalyst and maintained under a blanket or flow of inert gas adequate to provide an essentially oxygen free environment during conduct of the present process.

The temperature for conducting the process may be within a range of about 50° C. to 250° C. It is preferred that the temperature be within a range of about 50° C. to 200° C. Generally, higher temperatures allow the use of a lower concentration of supported aminoorganosilane, so the amount of supported aminoorganosilane employed will depend on the temperature at which the process is conducted.

The time required for conducting the process may vary depending on the particular silicon hydrides, unsaturated olefinic nitriles, and catalysts employed. In general, reaction times of 0.1 to 30 hours are useful. A preferred reaction time is in the range of about 0.5 to about 10 hours.

The following examples are given to illustrate the present invention. These examples are not intended to limit the instant claims.

EXAMPLE 1

Runs were conducted to evaluate the ability of various supported aminoorganosilanes to effect the addition of trichlorosilane to acrylonitrile to form beta-cyanoethyltrichlorosilane. The aminoorganosilanes were supported on Grade 57 silica gel from Davison Chemical of Baltimore, Md. The supported aminoorganosilanes evaluated in this study were:

1) N,N-dimethylaminopropyltrimethoxysilane, supported at a ratio of 11.72% weight percent of the weight of the silica gel, 2) N-methylaminopropyltrimethoxysilane, supported at 12.06% weight percent of the weight of the silica gel, 3) N'-methyl-N-piperazinylpropylmethyldimethoxysilane, supported at 11.52% weight percent of the weight of the silica gel, 4) N',N',-dimethylaminoethyl-N-methylaminopropyltrimethoxysilane, supported at 12.25% weight percent of the weight of the silica gel, and 5) N',N',-dimethylaminoethyl-N-methylaminopropyltrimethoxysilane, supported at 20.64% weight percent of the weight of the silica gel.

These supported aminoorganosilanes are represented by these numerical designations in this discussion and in Table 1.

The first step in preparing each supported aminoorganosilane was to remove free water from the silica gel by azeotroping. A mixture comprising approximately 40 g of silica gel and approximately 300-400 mL toluene was azeotroped for 2 hours at 108° C. in a reactor purged with argon. The aminoorganosilane was added to the azeotroped mixture comprising the silica gel and toluene. The quantities of aminoorganosilanes 1, 2, 3 and 4 which were added to the azeotroped mixture were those that would, in theory, result in the aminoorganosilanes being supported at 10 weight percent of the weight of the silica gel. The aminoorganosilanes 1, 2, 3, and 4 were actually supported on the silica gel at weight percents of 11.72, 12.06, 11.52, and 12.25, respectively, as shown above. The quantity of aminoorganosilane 5 added was that which, in theory, would result in the aminoorganosilane being supported at 30 weight percent of the silica gel. Aminoorganosilane 5 was actually supported at 20.64 weight percent of the weight of the silica gel, as shown above.

The mixture of silica gel, toluene and aminoorganosilane was refluxed for 7 to 18 hours.

Supported aminoorganosilanes 4 and 5 were then silylated by rinsing them with dry toluene and adding to them enough hexamethyldisilazane to cover the silica gel. The mixtures of supported aminoorganosilane and hexamethyldisilazane were heated to reflux, which was maintained for 5 hours with continuous stirring. Supported aminoorganosilanes 1, 2, and 3 were not silylated.

In an argon-purged atmosphere, all of the supported aminoorganosilanes were washed with toluene or hexane, then extracted with toluene or hexane in a Soxhlet extractor for at least 5 hours, washed again with toluene or hexane, and dried at room temperature for 6 hours under vacuum.

After preparation of the supported aminoorganosilanes, the comparative runs were conducted in sealed glass tubes purged with argon. The runs were conducted by placing a supported aminoorganosilane into each tube, then adding to each tube 2 mL of a mixture of trichlorosilane and acrylonitrile which had a molar ratio of 1.1 trichlorosilane to 1.0 acrylonitrile. The tubes were sealed then heated for 2 hours at 120° C. or 170° C., as indicated in Table 1.

The results of these runs are presented in Table 1. The content of individual tubes were analyzed by gas liquid chromatography(GLC) with a thermal conductivity detector(TCD). The results are expressed as the area percent(Area %) under the GLC-TCD trace for beta-cyanoethyltrichlorosilane, as a percentage of the total area under the GLC-TCD trace.

TABLE 1

Supported Aminoorganosilane Catalyzed Reaction of Trichlorosilane with Acrylonitrile at 120° C. and 170° C. for 2 hours

| Catalyst No. | Mole Ratio Aminoorganosilane/ Acrylonitrile | Area % beta-cyanoethyltrichlorosilane | |
|---|---|---|---|
| | | (120° C.) | (170° C.) |
| 1 | 0.032 | 56.6 | 80.1 |
| 2 | 0.032 | 1.4 | 59.6 |
| 3 | 0.016 | 13.7 | 78.4 |
| 4 | 0.016 | 32.4 | 76.6 |
| 5 | 0.016 | 18.8 | 79.0 |

EXAMPLE 2

Runs were conducted to evaluate the ability of a supported aminoorganosilane to effect the addition of trichlorosilane to acrylonitrile to form beta-cyanoethyltrichlorosilane, in the presence of a molar excess of trichlorosilane. The aminoorganosilane was supported on Grade 57 silica gel from Davison Chemical in the manner described in Example 1. The aminoorganosilane evaluated in these runs was N',N'-dimethylaminoethyl-N-methylaminopropyl- trimethoxysilane supported on silica gel.

Two samples of the aminoorganosilane were supported on silica gel, in a manner similar to that described in Example 1, at ratios of 20.19 and 20.64 weight percent of the weight of the silica gel, by adding a quantities of the aminoorganosilane which in theory would have resulted in supporting the aminoorganosilane at 30 weight percent of the weight of the silica gel. These are referred to in Table II as supported aminoorganosilane 6 and supported aminoorganosilane 7, respectively.

After supporting aminoorganosilane 7 onto silica gel, the supported aminoorganosilane 7 was silylated as described in Example 1. Supported aminoorganosilane 6 was not silylated.

The runs were conducted in sealed glass tubes purged with argon. The runs were conducted by adding 2 mL of a mixture of trichlorosilane and acrylonitrile to each tube containing a supported aminoorganosilane. The trichlorosilane was added to each tube in excess as described in Table 2. Tubes containing supported aminoorganosilanes 6 and 7 were then heated for 1.5 hours at a temperature in the range of 112°-118° C. Another tube containing supported aminoorganosilane 7 was heated for 1.5 hour at a temperature in the range of 165°-180° C.

The results of these runs are presented in Table 2. The contents of individual tubes were analyzed by GLC-TCD. The results are expressed as the area percent-(Area %) under the GLC-TCD trace for beta-cyanoethyltrichlorosilane, as a percentage of the total area under the GLC-TCD trace.

TABLE II

Supported Aminoorganosilane Catalyzed Reaction of Acrylonitrile with a Molar Excess of Trichlorosilane

| Catalyst No. | Mole Ratio Aminoorganosilane/ acrylonitrile | % Excess HSiCl₃ | Temperature °C. | Area % beta-cyanoethyltrichlorosilane |
|---|---|---|---|---|
| 6 | 0.044 | 51.9 | 112-118 | 67.2 |
| 7 | 0.061 | 51.9 | 112-118 | 73.6 |

TABLE II-continued

Supported Aminoorganosilane Catalyzed Reaction of Acrylonitrile with a Molar Excess of Trichlorosilane

| Catalyst No. | Mole Ratio Aminoorgano- silane/ acrylonitrile | % Excess HSiCl$_3$ | Tempera- ture °C. | Area % beta- cyanoethyl- trichloro- silane |
|---|---|---|---|---|
| 7 | 0.033 | 57.0 | 165–180 | 71.2 |

I claim:

1. A process for preparation of beta-cyanoalkylsilanes described by formula

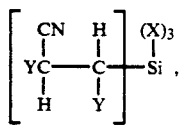

the process comprising:
contacting a silicon hydride described by formula $$HSiX_3$$

with an unsaturated olefinic nitrile described by formula

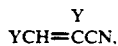

in the presence of a catalyst comprising an aminoorganosilane described by formula

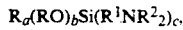

which is retained on a solid support; at a temperature within a range of about 50° C. to 250° C.; where each R is independently selected from a group consisting of monovalent hydrocarbon radicals of 1 to 20 carbon atoms; each R$^1$ is independently selected from a group consisting of bivalent hydrocarbon radicals of 1 to 20 carbon atoms; each R$^2$ is independently selected from a group consisting of hydrogen, monovalent hydrocarbon radicals of 1 to 20 carbon atoms, aminoalkyl radicals, alkylaminoalkyl radicals, alkylaminodialkyl radicals, dialkylaminoalkyl radicals, and polyaminoalkyl radicals; X is a halogen; each Y is independently selected from a group consisting of hydrogen and lower alkyl radicals of 1 to 8 carbon atoms; a=0, 1, 2, or 3; b=0, 1, 2, or 3; c=1, 2, 3, or 4; and
a+b+c=4.

2. A process according to claim 1, where the temperature is within a range of 50° C. to 200° C.

3. A process according to claim 1, where the halogen is chlorine.

4. A process according to claim 1, where the unsaturated olefinic nitrile is selected from a group consisting of acrylonitrile, methacrylonitrile, crotononitrile, ethylacrylonitrile, 1-cyanobutene-1, and 2-cyanooctene-1.

5. A process according to claim 1, where the unsaturated olefinic nitrile is acrylonitrile.

6. A process according to claim 1, where R of the aminoorganosilane is a lower alkyl radical.

7. A process according to claim 1, where R of the aminoorganosilane is phenyl.

8. A process according to claim 1, where at least one R$^2$ of the aminoorganosilane is methyl.

9. A process according to claim 1, where at least one R$^2$ of the aminoorganosilane is N'N'-dimethylaminoethyl.

10. A process according to claim 1, where one R$^2$ of the aminoorganosilane is methyl and one R of the aminoorganosilane is N'N'-dimethylaminoethyl.

11. A process according to claim 1, where the aminoorganosilane is selected from a group consisting of N,N-dimethylaminopropyltrimethoxysilane, N-methylaminopropyltrimethoxysilane, N'-methyl-N-piperazinylpropylmethyldimethoxysilane, N'-methyl-N-piperazinylpropyltrimethoxysilane, and N',N'- dimethylaminoethyl-N-methylaminopropyltrimethoxysilane.

12. A process according to claim 1, where the aminoorganosilane is selected from the group consisting of N,N-dimethylaminopropyltrimethoxysilane and N',N'-dimethylaminoethyl-N-methylaminopropyltrimethoxysilane, and the solid support is silica gel.

13. A process according to claim 1, where the aminoorganosilane is N',N'-dimethylaminoethyl-N-methylaminopropyltrimethoxysilane, the solid support is silica gel, and the aminoorganosilane is supported on the silica gel in an amount in the range of about 1 to 25 weight percent of the weight of the silica gel.

14. A process according to claim 1, where the beta-cyanoalkylsilane is beta-cyanoethyltrichlorosilane.

15. A process according to claim 1, where the silicon hydride is trichlorosilane, the olefinic nitrile is acrylonitrile, the aminoorganosilane is selected from a group consisting of N,N-dimethylaminopropyltrimethoxysilane and N',N'-dimethylaminoethyl-N-methylaminopropyltrimethoxysilane, the solid support is silica gel, and the temperature is within a range of about 100° C. to 170° C.

16. A process according to claim 1, where the mole ratio of of aminoorganosilane to unsaturated olefinic nitrile is in the range of about 0.010 to 0.7.

17. A process according to claim 1, where the mole ratio of silicon hydride to olefinic nitrile is about 1.0.

18. A process according to claim 1, where the process is run in an essentially oxygen free environment.

19. A process according to claim 18, where the essentially oxygen free environment contains less than about 0.5 percent free oxygen.

20. A process according to claim 1, where the supported aminoorganosilane is silylated.

21. A process according to claim 20, where the silylating agent is hexamethyldisilazane.

22. A process according to claim 1, where the process is conducted under heterogeneous conditions in a continuous-flow pressure coil.

23. A process according to claim 1, where the process is conducted for a time period in a range of about 0.1 to 30 hours.

24. A process according to claim 23, where the process is conducted for a time period in a range of about 0.5 to 10 hours.

25. A process according to claim 1, where the solid support is selected from a group consisting of silica gel, aluminum oxide, mixtures of aluminum oxide and chromium oxide, sodium zeolite, mixtures of aluminum oxide and tungsten oxide, magnesium oxide, zinc oxide, titanium oxide, asbestos, magnesium silicate, aluminum silicate, calcium silicate, and glass.

26. A process according to claim 1, where the solid support is silica gel.

* * * * *